United States Patent [19]
Okanishi et al.

[11] Patent Number: 5,478,813
[45] Date of Patent: Dec. 26, 1995

[54] ANTITUMOR SUBSTANCE BE-13793C DERIVATIVES

[75] Inventors: Masanori Okanishi, Tokyo; Daisuke Uemura, Shizuoka; Seiichi Tanaka, Tokyo; Katsuhisa Kojiri, Tokyo; Akira Okura, Tokyo; Kohtaro Funaishi, Okazaki; Hiroyuki Suda, Tokyo, all of Japan

[73] Assignee: Banyu Pharmaceutical Co., Ltd., Tokyo, Japan

[21] Appl. No.: 388,185

[22] Filed: Feb. 13, 1995

Related U.S. Application Data

[63] Continuation of Ser. No. 946,482, Nov. 10, 1992, abandoned.

[30] Foreign Application Priority Data

May 11, 1990 [JP] Japan .................... 2-122291

[51] Int. Cl.$^6$ .................................. C07H 19/23
[52] U.S. Cl. ............................. 514/43; 514/42; 536/16.8; 536/22.1; 536/27.1
[58] Field of Search .................. 536/16.8, 22.1, 536/27.1; 514/42, 43

[56] References Cited

U.S. PATENT DOCUMENTS

| | | | |
|---|---|---|---|
| 4,487,925 | 10/1984 | Lam et al. | 536/27.1 |
| 4,567,143 | 1/1986 | Matson | 435/119 |
| 4,785,085 | 11/1988 | Kareko et al. | 536/27.1 |
| 4,808,613 | 2/1989 | Kaneko et al. | 514/42 |
| 5,015,578 | 5/1991 | Schroeder et al. | 435/119 |
| 5,043,335 | 8/1991 | Kleinschroth et al. | 514/211 |
| 5,106,864 | 4/1992 | Suda et al. | 514/410 |
| 5,158,938 | 10/1992 | Lam et al. | 514/42 |
| 5,217,885 | 6/1993 | Suda et al. | 435/119 |

FOREIGN PATENT DOCUMENTS

| | | |
|---|---|---|
| 0269025 | 6/1988 | European Pat. Off. . |
| 0388956 | 9/1990 | European Pat. Off. . |

OTHER PUBLICATIONS

JP-A-20277, Banyu Pharmaceut Co. Ltd., "Antitumor Substance BE-13793C" Jan. 1, 1991.
"Journal of Organic Chemistry", American Chemical Society, vol. 54, No. 4, Feb. 17, 1989, pp. 824–828.
J. Antibiotics vol. 44, No. 7, 723–728 (1991) Kojiri et al.
J. Antibiotics v. 45, No. 11, 1797–1798 (1992) Tanaka et al.

*Primary Examiner*—Douglas W. Robinson
*Assistant Examiner*—Kathleen Kahler Fonda
*Attorney, Agent, or Firm*—Sherman and Shalloway

[57] ABSTRACT

This invention relates to 12,13-dihydro-6H-indolo[2,3-a]pyrrolo[3,4-c]carbazole-5,7(6H)-dione derivatives represented by the following general formula, pharmaceutically acceptable salts thereof, a method for preparation thereof and a use thereof:

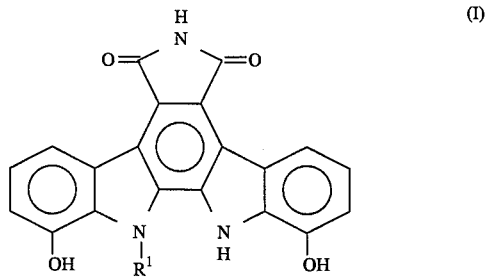

(I)

[wherein $R^1$ denotes a monosaccharide group having 5 to 7 carbon atoms, and the hydroxyl groups of this monosaccharide group can be replaced by the same or different 1 to 3 groups selected from the group consisting of a hydrogen atom, lower alkyl group, lower alkylcarbonyloxy group and lower alkoxy group.]

4 Claims, No Drawings

ANTITUMOR SUBSTANCE BE-13793C DERIVATIVES

This application is a continuation of application Ser. No. 07/946,482, filed Nov. 10, 1992 and now abandoned; which was the national phase entry of International Application No. PCT/JP91/00214, filed Feb. 20, 1991.

TECHNICAL FIELD

This invention is useful in the field of medicine, and relates more detailedly to novel BE-13793C (12,13-dihydro-1,11-dihydroxy-5H-indolo[2,3-a]pyrrolo[3,4-c]carbazole-5, 7(6H)-dione) derivatives inhibiting proliferation of tumor cells and exerting an antitumor effect, a method for preparation thereof and their use.

BACKGROUND ART

In the field of cancer chemotherapy, many compounds have already been put to practical use as medicine. However, their effects on various kinds of tumors are not necessarily adequate, and further the problem of resistance of tumor cells to these drugs makes the methods of clinical use thereof complicated [refer to Proceedings of the Japanese Cancer Association, 47 Annual Meeting, pages 12 to 15 (1988)].

In such state of things, development of novel carcinostatic substances is always desired in the field of cancer therapy. Particularly, substances are necessitated which overcome resistance of tumor cells against existing carcinostatic substances and exhibit effectiveness against such kinds of cancers that existing carcinostatic substances cannot exert adequate effects thereon.

In the light of such present state of things, the present inventors widely screened microbial metabolic products, as a result, found a novel antitumor activity-possessing compound BE-13793C (12,13-dihydro-1,11-dihydroxy-5H-indolo[2,3-a]pyrrolo[3,4-c]carbazole-5,7(6H)-dione), and disclosed it in the preceding patent application (Japanese Patent Application No. 71149/1989).

Further, the present inventors synthesized derivatives of BE-13793C, found that novel compounds represented by the later-described general formula (I) exhibited an excellent antitumor action, and completed this invention.

DISCLOSURE OF INVENTION

This invention relates to 12,13-dihydro-6H-indolo[2,3-a]pyrrolo[3,4-c]carbazole-5,7(6H)-dione derivatives represented by the following general formula, pharmaceutically acceptable salts thereof, a method for preparation thereof and a use thereof:

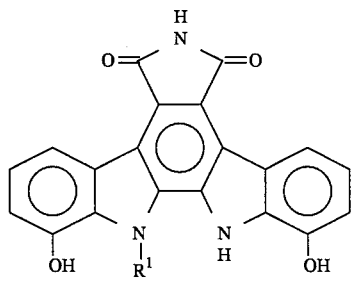

(I)

[wherein $R^1$ denotes a monosaccharide group having 5 to 7 carbon atoms, and the hydroxyl groups of this monosaccharide group can be replaced by the same or different 1 to 3 groups selected from the group consisting of a hydrogen atom, a lower alkyl group, lower alkylcarbonyloxy group and lower alkoxy group.]

The definitions of terminology used in this description are set forth below.

The monosaccharide group having 5 to 7 carbon atoms means a group obtained by removing an anomeric hydroxyl group from the cyclic form of a saccharide having 5 carbon atoms such as, for example, ribose, arabinose, xylose or lyxose, a saccharide having 6 carbon atoms such as, for example, allose, altrose, glucose, mannose, gulose, idose, galactose or talose, or a saccharide having 7 carbon atoms such as a heptose such as, for example, 7-sedoheptulose.

The term of "lower" means that the carbon number of the group or compound to which this term is attached is 5 or less. Therefore, a lower alkyl group means an alkyl group having 1 to 5 carbon atoms such as, for example, a methyl group, ethyl group, propyl group, isopropyl group, butyl group, isobutyl group, pentyl group or isopentyl group.

A lower alkylcarbonyloxy group means an alkylcarbonyloxy group having 1 to 5 carbon atoms such as an acetyloxy group, propionyloxy group, isopropionyloxy group, butanoyloxy group, isobutanoyloxy group, pentanoyloxy group or isopentanoyloxy group.

A lower alkoxy group means an alkoxy group having 1 to 5 carbon atoms such as, for example, a methoxy group, ethoxy group, propoxy group, isopropoxy group, butoxy group, isobutoxy group, pentyloxy group or isopentyloxy group, and a leaving group means a halogen atom such as a chlorine atom, bromine atom or iodine atom, or an alkylsulfonyloxy group or arylsulfonyloxy group such as a methanesulfonyloxy group or toluenesulfonyloxy group.

A method for preparation of compounds of the present invention is described below. A compound of this invention is prepared using as a starting raw material substance a novel antitumor substance BE-13793C [12,13- dihydro-1,11-dihydroxy-5H-indolo[2,3-a]pyrrolo[3,4-c]carbazole-5,7(6H)-dione; refer to Japanese Patent Application No. 71543/1990] represented by the following formula and disclosed in the preceding patent application:

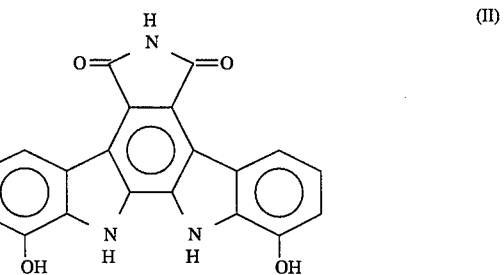

(II)

Namely, a compound of this invention is prepared by carrying out one or more of the following steps:

1) a step to react, in the presence of a base, the compound represented by the formula (II) or a compound B-(II) wherein an appropriate protective group is introduced in compound (II) with a compound represented by the general formula $$R^1-Z \qquad (III)$$

[wherein Z denotes a leaving group and $R^1$ has the same meaning as mentioned above] or a compound B-(III) wherein an appropriate protective group is introduced in $R^1$ of compound (III), and 2) a step to remove the protective group(s), and if necessary, converting the resultant compound into a pharmaceutically acceptable salt.

The reaction of compound (II) or B-(II) with compound (III) or B-(III) is usually carried out in a solvent which has no bad influence on the reaction, using a suitable base. Such a solvent includes an alcohol such as, for example, methanol, ethanol, propanol or isopropanol, ketones such as, for example, acetone or methyl isobutyl ketone, ethers such as, for example, tetrahydrofuran or dioxane, or an aprotic polar solvent such as, for example, N,N-dimethylformamide, acetonitrile or dimethyl sulfoxide, or a mixed solvent thereof, or a mixed solvent thereof with water. Further, a usable suitable base includes an alkali metal carbonate salt such as sodium bicarbonate, potassium bicarbonate, sodium carbonate or potassium carbonate, an alkali metal hydroxide such as sodium hydroxide or potassium hydroxide, an alkali metal hydride such as sodium hydride or lithium hydride, or the like.

In carrying out this condensation reaction, 1 to 3 moles of compound (III) or B-(III) is usually used per mole of compound (II) or compound B-(II). Further, if necessary, it is also possible to use compound (III) or B-(III) in an equimolar or less amount.

The use amount of the base is equimolar or excessive amount per the raw material compound, and usually 1 to 4 moles.

The reaction temperature is in the range of 0° C. to the boiling point of the solvent, preferably 0° C. to 100° C., and the reaction time is not particularly limited, but usually 0.5 to 24 hours.

Further, it is advantageous for smooth and efficient progress of the reaction to carry out, if necessary, the reaction under an atmosphere of an inert gas such as nitrogen or argon.

Introduction and removal of protective groups can be carried out selecting suitable protective groups and using methods used conventionally in this field (refer to T. W. Greene, Protective Groups in Organic Synthesis, John Wiley & Sons, 1981).

For example as for hydroxyl groups at the 1- and 11-positions, an alkanoyl group such as an acetyl group, a methoxymethyl group, a benzyl group or the like is used as a protective group, and particularly, a benzyl group is preferably used. Introduction of such a protective group can readily be made by reacting a corresponding halide with compound (II) in the presence of a base, and elimination of such a protective group can readily be made by acid or alkali hydrolysis or ammonolysis on an alkanoyl group and by hydrolysis with an acid catalyst, or the like on a methoxymethyl group, and can readily be made on a benzyl group, for example, by hydrogenation reaction using palladium-carbon as a catalyst. Further, as for protection of the imino group at the 6-position, a benzyloxymethyl group or the like is preferably used, introduction of this protective group can readily be made by reacting a compound wherein the hydroxyl groups of compound (II) are protected, with a benzyloxymethyl halide in the presence of a base, an elimination of this protective group can readily be made, for example, by carrying out catalytic hydrogenation reaction using palladium-carbon as a catalyst and treating the formed hydroxymethyl compound with concentrated ammonia water.

Further, as a protective group of the hydroxyl groups of a compound (III), an acetyl group is, for example, preferably used, this acetyl compound can readily be obtained by reacting the corresponding saccharide with an acid anhydride such as acetic anhydride in the presence of a base such as, for example, pyridine, and deacetylation can readily be made by reaction with a base such as sodium hydroxide or concentrated ammonia water. Further, as for a primary hydroxyl group, for example the hydroxyl group at the 6-position of a glucopyranosyl group, a triphenylmethyl group or the like is also preferably used. Introduction and elimination of this triphenylmethyl group can be made by a usual method well known in this field (refer to the aforementioned T. W. Greene, Protective Groups in Organic Chemistry, John Wiley & Sons page 34 to 35).

Compound (II), a raw material for preparation of compounds of this invention, can be prepared by the process (refer to Reference example) disclosed in the preceding Japanese Patent Application No. 71543/1990, and a compound represented by the general formula (III) or if necessary, compound B-(III) wherein the hydroxyl groups thereof are protected, which is another raw material, can be prepared by converting the anomeric hydroxyl group of a naturally occurred saccharide into a leaving group such as a halogen atom, or by converting a naturally occurred saccharide into a dehydroxyl compound, alkoxy compound, alkanoyl compound or alkyl compound by a well-known chemical process and then converting the anomeric hydroxyl group thereof into a leaving group such as a halogen atom [refer to J. W. Gillard et al., Tetrahedron Letters, 22, 513–616 (1981)].

Isolation and purification of the product of the above condensation reaction can be carried out by a method known in this field, for example, by solvent extraction, recrystallization or chromatography.

Further, the step to convert a compound obtained in the above step into a pharmaceutically acceptable salt can be carried out, for example, by applying a technique conventionally used in this field to the free compound prepared by the above preparation process.

Specific examples of these pharmaceutically acceptable salts are, for example, alkali metal salts such as a sodium salt and a potassium salt, alkaline earth metal salts such as a calcium salt, etc.

Compounds of this invention represented by the general formula (I) are useful compounds which exhibit an excellent proliferation inhibition activity against various cancer cells and are expected to be used as antitumor agents.

For demonstrating the above thing, a pharmacological test example is set forth below. In this connection was used as a control compound BE-13793C (12,13-dihydro-1,11-dihydroxy-5H-indolo[2,3-a]pyrrolo[3,4-c]carbazole-5,7(6H)-dione, refer to Japanese Patent Application 71543/1990).

Antitumor action (1) Preparation of test solutions

A test compound (20 mg) was dissolved in dimethyl sulfoxide (1 ml) and successively diluted into test solutions.

(2) Cancer cell-culturing media

DMEM medium containing 10% fetal bovine serum was used for a human gastric cancer cell MKN45 and a human colon cancer cell LS180, and RPMI-160 medium containing 10% fetal bovine serum was used for human lung cancer PC13.

(3) Measurement method

100 µl portions of the cell-culturing medium containing $3 \times 10^3$ cancer cells were put in a 96-hole microplate, culture was carried out under 5% $CO_2$ at 37° C. for 24 hours, 11 µl portions of the above test solution were added, the mixtures were subjected to culture under 5% $CO_2$ at 37° C. for further 72 hours, and then the cells were fixated with 50% trichloroacetic acid and stained with 0.4% sulforhodamine B. The dye was extracted from the stained cells with 10 mM Tris solution, and absorbance at 540 nm was measured and compared with that in the control group. As a result, the compound of this invention remarkably inhibited proliferation of the human cancer cells. Concentrations (IC$_{50}$) at which proliferation of the cancer cells was inhibited by 50% were measured, and listed in Table 1.

TABLE 1

| Kind of cell | IC$_{50}$ (μg/ml) | |
| --- | --- | --- |
| | Compound of Example 1 | BE-13793C |
| MKN45 | 0.28 | >50 |
| LS180 | 1.65 | >50 |
| PC13 | 1.70 | 12.5 |

As is seen from the foregoing, the compounds of this invention remarkably inhibit proliferation of human gastric cancer cells, colon cancer cells and lung cancer cells, and thus are expected to be clinically usable as antitumor agents.

As administration forms at the time of use of a compound of this invention, various forms can be selected, and there can be mentioned oral agents such as, for example, tablets, capsuls, powders, granules or liquids, or sterilized liquid parenteral agents such as, for example, solutions or suspensions.

Solid preparations can be prepared, as they are, as forms of tablets, capsuls, granules or powders, or can also be prepared using suitable additives. Such additives may be additives usually used, and include saccharides such as, for example, lactose and glucose; starches such as, for example, corn, wheat and rice; fatty acids such as, for example, stearic acid; inorganic salts such as, for example, aluminium magnesium metasilicate and anhydrous calcium phosphate; synthesized polymers such as, for example, polyvinylpyrrolidone and polyalkylene glycol; fatty acid salts such as, for example, calcium stearate and magnesium stearate; alcohols such as, for example, stearyl alcohol and benzyl alcohol; synthesized cellulose derivatives such as, for example, methylcellulose, carboxymethylcellulose, ethylcellulose and hydroxypropylmethylcellulose; and further, water, gelatin, talc, vegetable oils, gum arabic, etc.

Solid preparations such as these tablets, capsuls, granules and powders contain an effective ingredient generally at 0.1–100 weight %, preferably at 5–100 weight %.

Liquid preparations are prepared in forms such as suspensions, syrups or injections using suitable additives usually used in liquid preparations such as water, alcohols or oils originated in vegetables such as, for example, soybean oil, peanut oil and sesame oil.

Particularly, solvents suitable in case of parenteral administration by intramuscular injection, intravenous injection or subcutaneous injection includes, for example, distilled water for injection, aqueous lidocaine hydrochloride solutions (for intramuscular injection), physiological saline, aqueous glucose solutions, ethanol, liquids for intravenous injection (e.g. aqueous solutions of citric acid and sodium citrate, etc.), electrolyte solutions (for intravenous drip and intravenous injection), etc., and their mixed solvents.

These injections can take such forms that powder itself or to which suitable additives were added is dissolved at the time of use, besides such forms that ingredients are dissolved in advance. Such an injection contains usually 0.1–10 weight %, preferably 1–5 weight % of the effective ingredient.

Further, a liquid agent of a suspension, syrup or the like for oral administration contains 0.5–10 weight % of the effective ingredient.

It should be noted that the actually preferred dose of the compounds of this invention changes according to the kind of a compound to be used, the kind and application frequency of the compounded composition, the specified site to be treated, hosts and tumors. For example, the dose per day and per one adult is 10 to 500 mg in case of oral administration, and 10 to 100 mg per day in case of parenteral administration, preferably intravenous injection. The administration frequency varies depending on administration methods and symptoms, but is 1 to 5 times.

This invention is more specifically described below according to examples, but not limited only to these examples.

EXAMPLE 1

12,13-dihydro-1,11-dihydroxy-13-(β-D-glucopyranosyl)-5H-indolo[2,3-a]pyrrolo[3,4-c]carbazole-5,7(6H)-dione a) 180.5 mg of BE-13793C (12,13-dihydro-1,11-dihydroxy-5H-indolo[2,3-a]pyrrolo[3,4-c]carbazole-5,7-(6H)-dione) was dissolved in 137 ml of N,N-dimethylformamide (DMF), 510 mg of potassium carbonate was added, and 170 μl of benzyl bromide was added under ice cooling. The reaction solution was stirred at room temperature for 2 hours and, after addition of 200 ml of water, extracted with 200 ml of ethyl acetate, and the extract was dried over sodium sulfate and concentrated under reduced pressure to give 1,11-dibenzyloxy-12,13-dihydro-5H-indolo[[2,3-a]pyrrolo[3,4-c]carbazole-5,7(6H)-dione (yield: 93.7%).

Rf value 0.6 (chloroform-ethyl acetate (19:1))

b) 143.8 mg of 1,11-dibenzyloxy-12,13-dihydro-5H-indolo[2,3-a]pyrrolo[3,4-c]carbazole-5,7(6H)-dione was dissolved in 50 ml of DMF, 128.8 mg of 60% oily sodium hydride (NaH) was added, 36.5 μl of benzyloxymethyl chloride was gradually added under ice cooling over a period of 10 minutes, and the mixture was subjected to reaction at 0° C. for further 1 hour. The reaction solution was diluted with water and extracted with ethyl acetate, the ethyl acetate layer was dried over sodium sulfate and concentrated under reduced pressure, and the residue was purified by silica gel column chromatography (Kiezel gel 60; eluted with chloroform) to give the desired 6-benzyloxymethyl-1,11-dibenzyloxy-12,13-dihydro-5H-indolo[2,3-a]pyrrolo[3,4-c]carbazole-5,7(6H)-dione (yield: 61.7%).

Rf value 0.3 (chloroform)

c) To 5.4 mg of 6-benzyloxymethyl-1,11-dibenzyloxy-12,13-dihydro-5H-indolo[2,3-a]pyrrolo[3,4-c]carbazole-5,7(6H)-dione obtained by the operation of b) were added 5 ml of benzene, 51.6 mg of 1-bromotetraacetylglucose and 42.2 mg of silver oxide, and the mixture was refluxed with heating for 2 hours. After the reaction, the insoluble matters were removed by filtration, and the desired product was purified by column chromatography on silica gel (Kiesel gel 60; eluted with chloroform) to give 6-benzyloxymethyl-1,11-dibenzyloxy-12,13-dihydro-13-(tetraacetyl-β-D-glucopyranosyl)-5H-indolo[2,3-a]pyrrolo[3,4-c]carbazole-5,7(6H)-dione (yield: 34.8%)

Rf value 0.25 (chloroform)

d) To 4.5 mg of 6-benzyloxymethyl-1,11-dibenzyloxy-12,13-dihydro-13-(tetraacetyl-β-D-glucopyranosyl)-5H-indolo[2,3-a]pyrrolo[3,4-c]carbazole-5,7(6H)-dione were added 1.5 ml of ethyl acetate and 9 ml of ethanol to make a solution, and the solution was subjected to hydrogenation reaction in the presence of palladium-carbon catalyst (two medical spoonsful) for 3 hours. After the reaction, the palladium-carbon was removed by filtration and washed with methanol and tetrahydrofuran. The filtrate and the washings were concentrated under reduced pressure, the residue was subjected to thin layer chromatography (Kiesel gel 60; developed with chloroform-methanol=19:1), and the desired product was scraped and extracted with methanol to give 12,13-dihydro-1,11-dihydroxy-6-hydroxymethyl-13-(tetraacetyl-β-D-glucopyranosyl)-5H-indolo[2,3-a]pyrrolo[3,4-c]carbazole-5,7(6H)-dione (yield: 57.7%).

Rf value 0.3 (chloroform-methanol (19:1))

e) 4 mg of 12,13-dihydro-1,11-dihydroxy-6-hydroxymethyl-13-(tetraacetyl-β-D-glucopyranosyl)-5H-indolo[2,3-a]pyrrolo[3,4-c]carbazole-5,7(6H)-dione obtained by carrying out the operation of d) was dissolved in 5 ml of methanol, 4 ml of concentrated ammonia water was added, and, after stirring at room temperature for 4 hours, the solvent was distilled away under reduced pressure. The desired captioned compound, 12,13-dihydro-1,11-dihydroxy-13-(β-D-glucopyranosyl)-5H-indolo[2,3-a]pyrrolo[3,4-c]carbazole-5,7(6H)-dione was quantitatively obtained.

Rf value 0.32 (chloroform-methanol=2:1) 0.15 (chloroform-methanol-tetrahydrofuran=4:1:1)

FAB-MS (m/z): 520 [M+H]$^+$ $^1$H-NMR (300 MHz, DMSO-D$_6$), (ppm): 3.48 (1H,m), 3.64 (2H,m), 3.74 (1H,m), 4.02 (2H,m), 4.88 (1H,brd,J=5.3 Hz), 5.19 (1H,brd,J=5.3 Hz), 5.35 (1H,brt,J=5.0 Hz), 5.41 (1H,brd,J=5.6 Hz), 6.99 (1H,d,J=8.0 Hz), 7.03 (1H,d,J=8.0 Hz), 7.05 (1H,d,J=9.4 Hz), 7.17 (2H,t,J=8.0 Hz), 8.52 (1H, d,J=8.0 Hz), 8.70 (1H,d,J=8.0 Hz), 9.91 (1H,brs), 10.31 (1H,brs), 10.91 (1H,brs), 11.04 (1H,brs)

EXAMPLE 2

12,13-dihydro-1,11-dihydroxy-13-(β-D-galactopyranosyl)-5H-indolo[2,3-a]pyrrolo[3,4-c]carbazole-5,7(6H)-dione a) To 100 mg of 6-benzyloxymethyl-1,11-dibenzyloxy-12,13-dihydro-5H-indolo[2,3-a]pyrrolo[3,4-c[carbazole-5,7(6H)-dione) obtained by the operation of b) in Example 1 were added 50 ml of benzene, 940 mg of 1-bromotetraacetylgalactose and 1.41 g of silver oxide, and the mixture was refluxed with heating for 4 hours. After the reaction, the insoluble matters were removed by filtration, and the desired product was purified by silica gel column chromatography (Kiesel gel 60; eluted with n-hexane-ethyl acetate=3:1 and toluene-ethyl acetate=0:1) to give 51.3 mg of 6-benzyloxymethyl-1,11-dibenzyloxy-12,13-dihydro-13-(tetraacetyl-β-D-galactopyranosyl)-5H-indolo[2,3-a]pyrrolo[3,4-c]carbazole-5,7(6H)-dione as yellow solid (yield: 34.2%).

Rf value: 0.24 (n-hexanel-ethyl acetate (2:1))

b) To 49.8 mg of 6-benzyloxymethyl-1,11-dibenzyloxy-12,13-dihydro-13-(tetraacetyl-β-D-galactopyranosyl)-5H-indolo[2,3-a]pyrrolo[3,4-c]carbazole-5,7(6H)-dione obtained by the operation of a) were added 2 ml of ethyl acetate, 12 ml of ethanol and a catalytic amount of palladium black, and hydrogenation reaction was carried out for 2 hours. After the reaction, the palladium black was removed by filtration and the filtrate was concentrated under reduced pressure. 3 ml of methanol and 2.4 ml of concentrated ammonia water were added to the residue, the mixture was stirred at room temperature for 2 hours, and the solvent was distilled away. A small amount of tetrahydrofuran was added to the residue and the tetrahydrofuran-soluble part was subjected to column chromatography on Sephadex LH-20 (eluted with tetrahydrofuran). The desired product-containing fraction was collected, the solvent was distilled away, and the resultant reddish yellow solid was washed with diethyl ether to give 17.2 mg of the desired captioned compound, 12,13-dihydro-1,11-dihydroxy-13-(β-D-galactopyranosyl)-5H-indolo[2,3-a]pyrrolo[3,4-c]carbazole-5,7(6H)-dione as reddish yellow solid (yield: 65.7%).

Rf value: 0.18 (ethyl acetate-methanol (5:1))

FAB-MS (m/z): 519 [M]$^+$ $^1$H-NMR (300 MHz, CD$_3$OD), (ppm): 3.78 (1H,dd,J=3.0 Hz,9.3 Hz), 4.08 (2H,m), 4.17 (1H,m), 4.24 (1H,d,J=3.0 Hz), 4.29 (1H,t,J=9.3 Hz), 6.95 (1H,dd,J=1.2 Hz, 7.8 Hz), 6.98 (1H,dd,J=1.2 Hz,7.8 Hz), 7.11 (1H,t,J=7.8 Hz), 7.14 (1H ,t,J=7.8 Hz), 7.24 (1H,d,J=9.3 Hz), 8.65 (1H,dd,J= 1.2Hz,7.8 Hz), 8.83 (1H,dd,J=1.2 Hz,7.8 Hz)

Reference Example

Any microorganism or its mutant can be used as one used to produce BE-13793C represented by the formula (II), a raw material compound of compounds of this invention, so long as it is capable of producing an antitumor substance BE-13793C, and for example there can be mentioned BA-13793 strain [Fermentation Research Institute, Agency of Industrial Science and Technology, the Ministry of International Trade and Industry (Bikoken); Accession No.: FERM P-10489); This strain was transferred to international deposition and its accession number is FERM BP-2785)]. A process of preparation of BE-13793C using this strain is, for example, as follows.

BA-13793 strain cultured on a slant agar medium was inoculated into 100 ml of a medium (pH 6.7) comprising 0.1% glucose, 2.0% dextrin, 1.0% corn gluten meal, 0.5% fish meal, 0.1% yeast extract, 0.1% sodium chloride, 0.05% magnesium sulfate, 0.05% calcium chloride, 0.0002% ferrous sulfate, 0.00004% cupric chloride, 0.00004% manganese chloride, 0.00004% cobalt chloride, 0.00008% zinc sulfate, 0.00008% sodium borate, 0.00024% ammonium molybdate and 0.5% 3-(N-morpholino)propanesulfonic acid in each of four 500-ml culturing Erlenmeyer flasks, and cultured at 28° C. for 72 hours on a rotary shaker (180 r.p.m.). 1 ml of the resulted culture broth was inoculated into 100 ml of the above-described medium in each of fifty 500-ml culturing Erlenmeyer flasks, and cultured at 28° C. for 120 hours on a rotary shaker (180 r.p.m.). The culture broth (about 5 l) was filtered by filtration, the resultant cells were washed with 500 ml of deionized water, and then 2.5 l of methanol was added to the cells and the mixture was stirred at room temperature for 1 hour. Then methanol extract was obtained by filtration. Methanol extraction was carried out one more time, and the combined methanol extract (about 5 l) was concentrated up to about 800 ml under reduced pressure. The resultant concentrate was extracted with 3 l of ethyl acetate, the ethyl acetate extract was concentrated under reduced pressure, and the resultant residue was washed with 500 ml of chloroform added to give 720 mg of a BE-13793C-containing crude substance. This crude substance was dissolved in 2 l of methanol, the solution was concentrated under reduced pressure to form an orange precipitate, and this was taken to give 546 mg of a BE-13793C-containing substance. This substance was dissolved in a mixed solvent of methanol-tetrahydrofuran=1:1 (v/v), the solution was subjected to column chromatography on Sephadex LH-20 (produced by Pharmacia Co.) (1.5×120 cm), development was made using methanol-tetrahydrofuran=1:1 (v/v), and the resultant BE-13793C fraction was concentrated under reduced pressure to give 99 mg of BE-13793C as a yellowish orange crystalline substance.

Industrially Applicable Field

This invention is useful in the filed of medicine, and more detailedly, relates to novel BE-13793C (12,13-dihydro-1,11-dihydroxy-5H-indolo[2,3-a]pyrrolo-[3,4-c]carbazole-5,7(6H)-dione) derivatives which inhibit proliferation of tumor cells and exert an antitumor effect, a process for preparation thereof and a use thereof.

We claim:

1. A BE-13793C derivative of the formula (I) or a pharmaceutically acceptable salt thereof

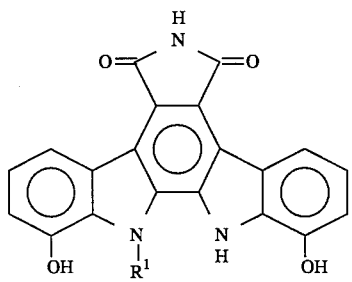

wherein R' is a monosaccharide group having 5 to 7 carbon atoms.

2. A pharmaceutical composition comprising an antitumor effective amount of the BE-13793C derivative of formula (I) set forth in claim 1 or a pharmaceutically acceptable salt thereof and an adjuvant.

3. 12,13-Dihydro-1,11-dihydroxy-13-($\beta$-D-glucopyranosyl)-5H-indolo[2,3-a]pyrrolo[3,4-c]carbazole-5,7(6H)-dione, or 12,13-dihydro-1,11-dihydroxy-13-($\beta$-D-galactopyranosyl)-5H-indolo[2,3-a]pyrrolo[3,4c]carbazole-5,7(6H)-dione.

4. A BE-13793C derivative of the formula (IA) or a pharmaceutically acceptable salt thereof

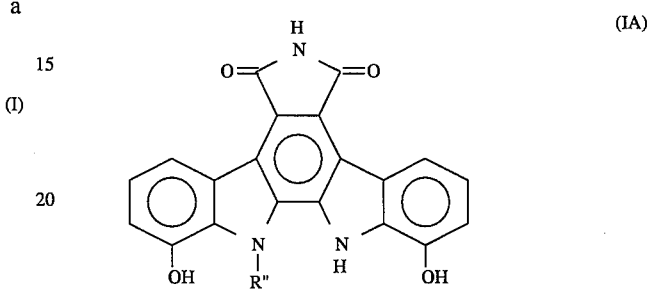

wherein R" is ribosyl, arabinosyl, xylosyl, lyxosyl, allosyl, altrosyl, glucosyl, mannosyl, gulosyl, idosyl, galactosyl, talosyl or 7-sedoheptulosyl.

* * * * *